(12) United States Patent
Spencer Jones et al.

(10) Patent No.: US 8,998,912 B2
(45) Date of Patent: Apr. 7, 2015

(54) CLAMPING PATELLA DRILL GUIDE

(75) Inventors: Richard Spencer Jones, Shrewsbury (GB); Martin W. Roche, Ft. Lauderdale, FL (US); Abraham P. Wright, Winona Lake, IN (US)

(73) Assignee: Depuy (Ireland), Cork (IE)

( * ) Notice: Subject to any disclaimer, the term of this patent is extended or adjusted under 35 U.S.C. 154(b) by 390 days.

(21) Appl. No.: 13/548,647

(22) Filed: Jul. 13, 2012

(65) Prior Publication Data

US 2013/0079788 A1 Mar. 28, 2013

Related U.S. Application Data

(60) Provisional application No. 61/540,049, filed on Sep. 28, 2011.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61B 17/17* | (2006.01) |

(Continued)

(52) U.S. Cl.
CPC ............. *A61F 2/4684* (2013.01); *A61F 2/3877* (2013.01); *A61B 17/1767* (2013.01); *A61F 2002/30225* (2013.01); *A61F 2002/30227* (2013.01); *A61F 2002/30616* (2013.01); *A61F 2002/30878* (2013.01); *A61F 2002/30892* (2013.01); *A61B 17/8866* (2013.01)

(58) Field of Classification Search
CPC ............. A61B 17/158; A61B 17/1767; A61B 17/1677; A61B 2019/304

USPC ................... 606/79, 80, 86 R, 87–88, 96–98, 606/205–209

See application file for complete search history.

(56) References Cited

U.S. PATENT DOCUMENTS

| 2,181,746 A | 11/1939 | Siebrandt |
| 3,835,849 A | 9/1974 | McGuire |

(Continued)

FOREIGN PATENT DOCUMENTS

| EP | 791335 A1 | 8/1997 |
| EP | 992222 A2 | 4/2000 |

(Continued)

OTHER PUBLICATIONS

European Search Report, European Patent Application No. 12186675.0-2310, Dated Dec. 12, 2012 (7 Pages).

(Continued)

*Primary Examiner* — David Bates
*Assistant Examiner* — Samuel Hanna

(57) ABSTRACT

A patella drill guide includes a base with a flat patella bone-facing surface, a drill guide bore extending through the base, a cantilever spring member and a bone-gripping member. The cantilever spring member biases the bone-gripping member and the flat patella bone-facing surface toward each other. Flexing the cantilever spring member moves the bone-gripping member away from the flat patella bone-facing surface so that the drill guide can be placed on the patella. When the cantilever spring member is released, the patella is clamped between the bone-gripping member and the flat patella bone-facing surface. The drill guide may have sizing indicia and may be part of a kit including trial components to be mounted to the drill guide.

10 Claims, 6 Drawing Sheets

(51) Int. Cl.
*A61F 2/38* (2006.01)
*A61F 2/30* (2006.01)
*A61B 17/88* (2006.01)

(56) References Cited

U.S. PATENT DOCUMENTS

| | | | |
|---|---|---|---|
| D260,927 S | 9/1981 | Glenn | |
| D281,622 S | 12/1985 | Diamond | |
| 4,565,192 A | 1/1986 | Shapiro | |
| 4,633,862 A | 1/1987 | Petersen | |
| 5,002,547 A | 3/1991 | Poggie et al. | |
| 5,021,055 A | 6/1991 | Burkinshaw | |
| 5,108,401 A | 4/1992 | Insall et al. | |
| 5,116,338 A | 5/1992 | Poggie | |
| 5,129,907 A | 7/1992 | Heldreth | |
| 5,129,908 A | 7/1992 | Petersen | |
| 5,147,365 A | 9/1992 | Whitlock et al. | |
| 5,222,955 A | 6/1993 | Mikhail | |
| 5,250,050 A | 10/1993 | Poggie et al. | |
| 5,284,482 A | 2/1994 | Mikhail | |
| 5,284,485 A | 2/1994 | Kammerer et al. | |
| 5,312,409 A | 5/1994 | McLaughlin | |
| 5,382,254 A | 1/1995 | McGarry et al. | |
| 5,415,663 A | 5/1995 | Luckman et al. | |
| 5,470,328 A | 11/1995 | Furnish et al. | |
| 5,484,451 A | 1/1996 | Akopov et al. | |
| D367,531 S | 2/1996 | Price et al. | |
| 5,520,692 A | 5/1996 | Ferrante | |
| 5,536,271 A | 7/1996 | Daly | |
| 5,542,947 A | 8/1996 | Treacy | |
| D373,635 S | 9/1996 | Price et al. | |
| 5,575,793 A | 11/1996 | Carls et al. | |
| 5,582,615 A | 12/1996 | Foshee et al. | |
| 5,593,450 A | 1/1997 | Scott et al. | |
| 5,611,802 A | 3/1997 | Samuelson et al. | |
| 5,626,607 A | 5/1997 | Malecki et al. | |
| 5,667,512 A | 9/1997 | Johnson | |
| 5,716,362 A | 2/1998 | Treacy | |
| 5,827,279 A | 10/1998 | Hughett et al. | |
| 5,916,217 A * | 6/1999 | Manthrop et al. | 606/75 |
| 5,941,884 A | 8/1999 | Corvelli et al. | |
| 5,944,723 A | 8/1999 | Colleran | |
| 5,968,051 A | 10/1999 | Luckman et al. | |
| 6,010,509 A | 1/2000 | Delgado et al. | |
| 6,056,754 A | 5/2000 | Haines et al. | |
| 6,074,425 A | 6/2000 | Pappas | |
| 6,190,391 B1 | 2/2001 | Stubbs | |
| 6,205,884 B1 | 3/2001 | Foley et al. | |
| D459,474 S | 6/2002 | Bratt et al. | |
| 6,419,675 B1 | 7/2002 | Gallo, Sr. | |
| D463,550 S | 9/2002 | Sherman | |
| 6,855,150 B1 | 2/2005 | Linehan | |
| 6,866,667 B2 | 3/2005 | Wood et al. | |
| 6,923,812 B1 * | 8/2005 | Wellisz | 606/75 |
| D549,331 S | 8/2007 | Tomatsu et al. | |
| 7,344,540 B2 | 3/2008 | Smucker et al. | |
| 7,566,335 B1 | 7/2009 | Scott et al. | |
| 7,632,279 B2 | 12/2009 | Bastian | |
| 7,780,594 B2 | 8/2010 | Hutton | |
| 7,806,899 B2 | 10/2010 | Hogg et al. | |
| 7,878,989 B2 | 2/2011 | McMinn | |
| 7,891,071 B2 | 2/2011 | Collazo | |
| D634,011 S | 3/2011 | Phillips et al. | |
| D638,541 S | 5/2011 | Claypool | |
| 7,972,383 B2 | 7/2011 | Goldstein et al. | |
| D642,678 S | 8/2011 | Dockstader et al. | |
| D646,389 S | 10/2011 | Claypool et al. | |
| 8,216,242 B2 | 7/2012 | Marchyn | |
| D667,552 S | 9/2012 | Claypool | |
| D667,953 S | 9/2012 | Wright | |
| 2002/0115987 A1 | 8/2002 | Hildwein et al. | |
| 2003/0163137 A1 | 8/2003 | Smucker et al. | |
| 2004/0153066 A1 | 8/2004 | Coon | |
| 2004/0162561 A1 | 8/2004 | Marchyn | |
| 2005/0240196 A1 | 10/2005 | Davis et al. | |
| 2006/0142777 A1 | 6/2006 | Bastian | |
| 2007/0118141 A1 | 5/2007 | Marchyn et al. | |
| 2007/0233142 A1 | 10/2007 | Oliver | |
| 2007/0260227 A1 | 11/2007 | Phan | |
| 2008/0097450 A1 | 4/2008 | Brown et al. | |
| 2008/0114366 A1 | 5/2008 | Smucker et al. | |
| 2008/0177394 A1 | 7/2008 | Chauhan | |
| 2008/0228190 A1 | 9/2008 | Sherry et al. | |
| 2008/0306484 A1 | 12/2008 | Coon | |
| 2009/0264737 A1 | 10/2009 | Haechler et al. | |
| 2009/0326661 A1 | 12/2009 | Wright et al. | |
| 2010/0030223 A1 | 2/2010 | Kellar | |
| 2010/0152742 A1 | 6/2010 | Nevelös et al. | |
| 2010/0168753 A1 | 7/2010 | Edwards et al. | |
| 2011/0066193 A1 | 3/2011 | Lang | |
| 2012/0078261 A1 | 3/2012 | Kecman et al. | |
| 2013/0023883 A1 | 1/2013 | Wright | |
| 2013/0023890 A1 | 1/2013 | Kecman | |
| 2013/0030443 A1 | 1/2013 | Wright | |
| 2013/0030539 A1 | 1/2013 | Wright | |
| 2013/0035693 A1 | 2/2013 | Wright | |
| 2013/0079787 A1 | 3/2013 | Spencer Jones | |
| 2013/0079789 A1 | 3/2013 | Randle | |
| 2013/0211410 A1 | 8/2013 | Landes | |

FOREIGN PATENT DOCUMENTS

| | | | | |
|---|---|---|---|---|
| EP | 1723916 A1 | 11/2006 | | |
| EP | 1967143 A2 | 9/2008 | | |
| EP | 2574314 A1 | 4/2013 | | |
| FR | 2737848 | * | 2/1997 | A61F 2/46 |
| FR | 2737848 A1 | 2/1997 | | |
| WO | WO 9945856 A1 | 9/1999 | | |
| WO | WO 2005110249 A1 | 11/2005 | | |
| WO | WO 2008112996 A1 | 9/2008 | | |

OTHER PUBLICATIONS

European Search Report, European Patent Application No. 12186728.7-2310, Dated Dec. 14, 2012 (8 Pages).
European Search Report, European Patent Application No. 12186700.6-2310, Dec. 13, 2012 (8 Pages).
Australian Search Report for Patent Application No. 2012227341 Dated Jun. 13, 2014, 3 Pages.
DePuy International Ltd., PFC Sigma Rotating Platform Knee System with MBT Tray, Surgical Technique Brochure, 2003, (43 pages), Cat. No. 9068-96-000, DePuy International Ltd., Leeds, England.
DePuy Orthopaedics, Inc., LCS High Performance Instruments, Surgical Technique Guide, 2008, (44 pages), Pub. No. 0612-85-506, DePuy Orthopaedics, Inc., Warsaw, IN.
DePuy Orthopaedics, Inc., Sigma High Performance Instruments, Classic Surgical Technique, 2010, (52 pages), Pub. No. 0612-89-510, DePuy Orthopaedics, Inc., Warsaw, IN.
DePuy Orthopaedics, Inc., Sigma High Performance Instruments, Design Rationale, 2009, (12 pages), Pub. No. 0612-54-506 (Rev.2), DePuy Orthopaedics, Inc., Warsaw, IN.
European Search Report, European Patent Application No. 11175824.9-2310, Dec. 16, 2011, (8 pages).
European Search Report, European Patent Application No. 11175824.9-2310, Mar. 1, 2013 (7 pages).

* cited by examiner

CLAMPING PATELLA DRILL GUIDE

CROSS-REFERENCE TO RELATED APPLICATION

This application claims priority to U.S. Prov. App. No. 61/540,049 filed Sep. 28, 2011, entitled "Clamping Patella Drill Guide," which is incorporated by reference herein in its entirety.

TECHNICAL FIELD

The present disclosure relates generally to orthopaedic surgical instruments and more particularly to patella drill guides.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a patella replacement procedure, an orthopaedic prosthesis is implanted into the patient's patella. Specifically, a prosthetic patella implant component is secured to the patient's natural patella such that its posterior surface articulates with a femoral component during extension and flexion of the knee.

To facilitate the replacement of the articulating surface of the natural patella with the prosthetic patella, orthopaedic surgeons use a variety of orthopaedic surgical instruments such as, for example, saws, drills, mills or reamers to resect the posterior surface of the patella and then to prepare the resected surface for fixation of the prosthetic patella implant component.

Common fixation elements for prosthetic patellae include one or more pegs extending out from the bone-facing (anterior) surface to be received in complementary recesses or holes drilled or reamed into the patella. To prepare the patella to receive such a prosthetic patella, the surgeon generally resects the posterior portion of the patella to define a flat surface and then uses a drill guide and drill to drill the hole or holes into the resected surface of the patella. However, it is difficult to hold the patella drill guide stationary against the patella while drilling, particularly when the patella is everted: this surgical step may require one hand to hold the patella, another hand to hold the drill guide and a third hand to drill the holes.

In some prosthetic patella implants, the articulating surface of the prosthetic patella implant component is dome-shaped, as in U.S. Pat. No. 5,593,450. In other types of prosthetic patella implants, the articulating surface has an asymmetric shape to be received and track within the patellar groove in the prosthetic femoral implant component. An example of such an asymmetrically-shaped prosthetic patella implant component is disclosed in U.S. Pat. No. 6,074,425. With such asymmetric patella implants, rotational alignment of the implant impacts the way in which the patella implant tracks in the trochlear groove of the femoral implant. Such asymmetric patella implants typically include a plurality of pegs extending out from the anterior surface to be received in the complementary holes drilled in the patella surface. However, the surgeon typically cannot fully evaluate tracking of the patella implant complonent in the patellar groove of the femoral component until trial patellar and femoral components are in place, which generally requires that the complementary holes be drilled before the trial is placed on the resected patella. If the surgeon determines that the patella trial does not track correctly, there is little opportunity to make adjustments since the mounting holes have already been drilled into the resected patella surface.

SUMMARY

The present invention provides a patella drill guide that allows the surgeon to hold the patella and the patella drill guide together with a single hand while drilling with the other hand. Some embodiments also allow the surgeon to evaluate patella tracking prior to drilling the mounting holes.

In an illustrative embodiment, the present invention provides a patella drill guide for use in preparing a resected patellar bone surface to receive a prosthetic patellar implant, the patella drill guide comprising a handle, a base portion, a cantilever spring member and a bone-gripping member. The base portion extends from the handle to a free end having a flat patella bone-facing surface. A drill guide bore extends through the base portion to and through the flat patella bone-facing surface. The cantilever spring member has one end fixed to the handle and an opposite free end aligned with the flat patella bone-facing surface of the base portion. The bone-gripping member is at the free end of the cantilever spring member and has a portion extending outward from the cantilever spring member toward the flat patella bone-facing surface of the base portion. The patella drill guide also includes a deflector connected to the handle. The deflector engages a portion of the cantilever spring member between the two ends. The cantilever spring member has a relaxed position wherein there is a first distance between the bone-gripping member and the flat patella bone-facing surface. The cantilever spring member also has a deflected position wherein the bone-gripping member is spaced a second distance away from the flat patella bone-facing surface. The second distance is greater than the first distance. Activation of the deflector moves the bone-gripping member of the cantilever spring member from the relaxed position to the deflected position.

In a more particular embodiment, there are a plurality a drill guide bores extending through the base portion to and through the flat patella bone-facing surface.

In another more particular embodiment, the base portion has an edge around a part of its circumference and this edge includes a plurality of spaced recesses. In this embodiment, the base portion may have a top surface opposite the flat patella bone-facing surface, and the top surface may include sizing indicia adjacent to the spaced recesses.

In this embodiment, the thickness of the base portion may be greater around the drill guide bores than around the spaced recesses.

In another more particular embodiment, a trial articulation surface is opposite and spaced from the flat patella bone-facing surface. This trial articulation surface has a curved contour. In some embodiments, a plurality of spaced drill guide bores extend from the trial articulation surface through the base portion to and through the flat patella bone-facing surface.

In this embodiment, the trial articulation surface and the flat patella bone-facing surface may comprise discrete components assembled to define a combination patella drill guide and trial, or may alternatively comprise a single, unitary component.

In this embodiment, when the patella drill guide is mounted on a patella, the patella drill guide may be rotatable with respect to the patella about an axis extending through the bone-gripping member and the base portion.

In this embodiment, the axis of rotation may be substantially perpendicular to the plane of the flat patella bone-facing surface and substantially parallel to the central longitudinal axes of the drill guide bores.

In this embodiment, the patella drill guide may further comprise a bone-gripping component assembled with the base portion, and the base portion may be rotatable with respect to the bone-gripping component.

In this embodiment, the bone-gripping component on the base portion may comprise a plurality of spikes.

In this embodiment, the bone-gripping member at the free end of the cantilever spring member may also comprise a plurality of spikes.

In another embodiment, the bone-gripping member at the free end of the cantilever spring member comprises a pedestal and has a plurality of spikes extending outward from the pedestal. In this embodiment, the cantilever spring member is pivotably connected to the bone-gripping member so that the handle, the free end of the base portion and the cantilever spring member are pivotable with respect to the bone-gripping member.

In this embodiment, the base portion may have a top surface opposite and spaced from the flat patella bone-facing surface. This top surface may comprise a trial articulation surface having a curved contour. In this embodiment, the drill guide bore may extend from the trial articulation surface through the base portion to and through the flat patella bone-facing surface.

In this embodiment, there may be a plurality a spaced drill guide bores extending from the trial articulation surface through the base portion to and through the flat patella bone-facing surface.

In a particular embodiment, the first distance between the bone-gripping member and the flat patella bone-facing surface is greater than zero. In an alternative particular embodiment, the first distance between the bone-gripping member and the flat patella bone-facing surface is zero.

In another illustrative embodiment, the present invention provides a patella drill guide for use in preparing a resected patellar bone surface to receive a prosthetic patellar implant. In this illustrative embodiment, the patella drill guide comprises a base portion, a cantilever spring member and a bone gripping member. The base portion has a flat patella bone-facing surface and a drill guide bore extends through the base portion to and through the flat patella bone-facing surface. The bone-gripping member faces toward the flat patella bone-facing surface of the base portion. The cantilever spring member biases at least one of the bone-gripping member and the flat patella bone-facing surface in one direction. Flexing the cantilever spring member moves the biased element in another direction.

In a particular embodiment, there are a plurality of drill guide bores that extend through the base portion to and through the flat patella bone-facing surface.

In a particular embodiment, the base portion has an edge around a part of its circumference and this edge includes a plurality of spaced recesses.

In this embodiment, there may be sizing indicia on the top surface of the base adjacent to the spaced recesses. In a particular embodiment, the thickness of the base is greater around the drill guide bores than around the spaced recesses.

In a particular embodiment, a first arm extends outwardly from the base portion to an end and a second arm extends outwardly from the bone-gripping member to an end. In this embodiment, the first arm and the second arm are connected by a hinge and the cantilever spring member has one end fixed to one of the arms and another portion of the cantilever spring member bears against a portion of the other arm. Thus, the cantilever spring member biases the bone-gripping member and the flat patella bone-facing surface toward each other. When the cantilever spring member is flexed by squeezing the ends of the two arms together.

In another particular embodiment, the patella drill guide further comprises a handle and a deflector. In this embodiment, the cantilever spring member has one end mounted to the handle and an opposite free end. The bone-gripping member is at the free end of the cantilever spring member. The deflector is connected to the handle and engages a portion of the cantilever spring member between the two ends. Activation of the deflector flexes the cantilever spring member away from the patella bone-facing surface.

BRIEF DESCRIPTION OF THE DRAWINGS

The detailed description particularly refers to the following figures, in which.

DETAILED DESCRIPTION OF THE DRAWINGS

Figure 1:
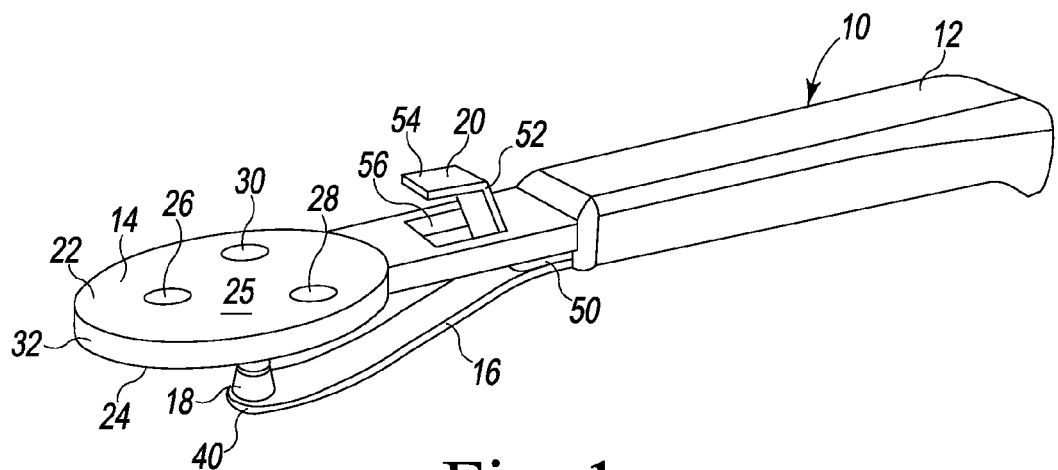
FIG. 1 is a perspective view of one embodiment of a patella drill guide incorporating the principles of the present invention.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, a first embodiment of a clamping patella drill guide 10 is illustrated. The illustrated patella drill guide 10 comprises a handle 12, a base portion 14, a cantilever spring member 16, a bone-gripping member 18 and a deflector 20.

The base portion 14 is connected to the handle 12 and extends from the handle 12 to a free end 22. The free end 22 has a flat patella bone-facing surface 24 and a top surface 25 spaced from the patella bone-facing surface 24; in the first illustrated embodiment, the top surface 25 and patella bone-facing surface 24 lie in parallel planes. A plurality of cylindrical drill guide bores 26, 28, 30 extend from the top surface 25, through the base portion 14 to and through the patella bone-facing surface 24. An edge 32 extends between the top surface 25 and the patella bone-facing surface 24.

As can be seen in FIG. 1, the bores 26, 28, 30 in the illustrated embodiment are spaced in a triangular pattern on the free end 22. The number of bores and spacing between the bores 26, 28, 30 correspond with the number and spacing of the mounting pegs on the patella implant component. The diameter of the bores corresponds generally with the diameters of the mounting pegs on the patella implant component. It should be understood that the number, spacing and size of the bores may be adjusted from the illustrated embodiment, depending on the number, spacing and sizes of the mounting pegs on the patella implant component.

Figure 4:
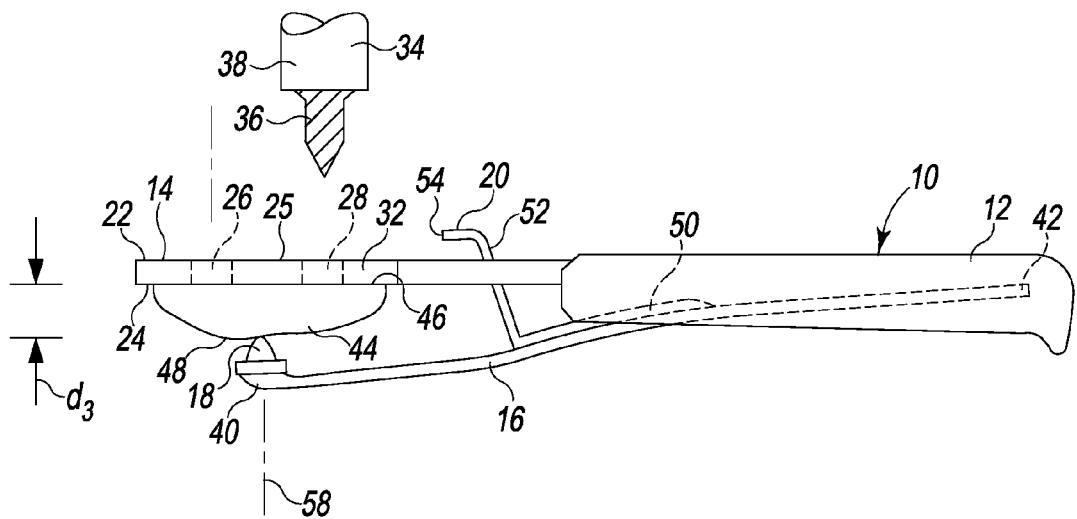
FIG. 4 is a side elevation view of the patella drill guide of FIGS. 1-3, shown clamping a resected patella.

FIG. 4 illustrates the first embodiment of the clamping patella drill guide together with a drill bit 34. The drill bit 34 has a fluted portion 36 that has a diameter corresponding with the diameter of the mounting pegs on the patella component; the fluted portion 36 may include a frusto-conical portion to form counter-sunk holes in the patella. The illustrated drill bit also has a collar portion 38 that has a diameter greater than the diameters of the bores 26, 28, 30. In use, the top surface 25 of the base portion surrounding the bores 26, 28, 30 serves as a stop for the collar portion 38 of the drill bit 34; the collar portion 38, thickness of the base portion 14 and the length of the fluted portion 36 of the drill bit thereby control the depth of the holes drilled into the patella. The depth generally corresponds with the lengths of mounting pegs on the patella implant component.

As shown in FIGS. 1-4, the patella bone-facing surface 24 of the base portion 14 overlies the bone-gripping member 18 at a free end 40 of the cantilever spring member 16. The opposite end 42 of the cantilever spring member 16 is fixed to the handle 12. In the embodiment illustrated in FIGS. 1-4, the bone-gripping member 18 comprises a single conical spike extending toward the patella bone-facing surface 24 of the base portion 14. This spike may be sharp enough so that its point can be pushed slightly into the anterior surface of the patella to firmly clamp the patella to the end 22 of the base portion 14 of the patella drill guide 10. In the illustrated embodiment, the cantilever spring member 16 is shaped so that the spike is aligned along an axis intersecting the plane of the patella bone-facing surface 24.

Figure 2:
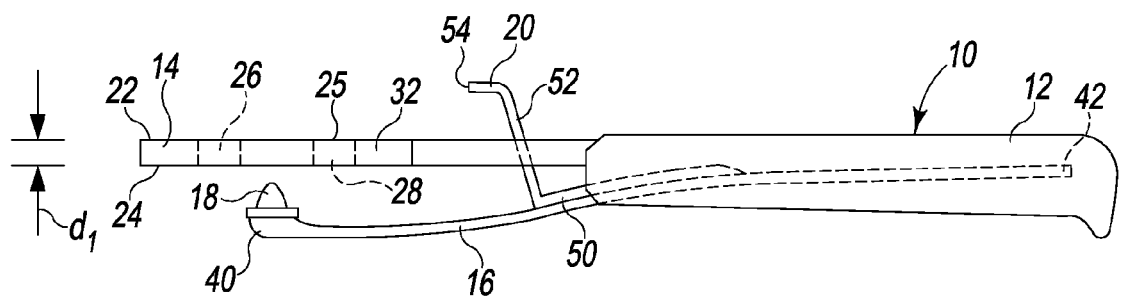
FIG. 2 is a side elevation view of the patella drill guide of FIG. 1.

As shown in FIGS. 1-2, the cantilever spring member 16 has a relaxed position wherein the bone-gripping member 18 is spaced a first distance away from the patella bone-facing surface 24. This first distance is shown at $d_1$ in FIG. 2. The cantilever spring member 16 is shaped to bias the bone-gripping member 18 toward the flat patella bone-facing surface 24. The free end 40 of the cantilever spring member 16 can be deflected to a variety of positions by flexing the cantilever spring member. For example, the free end 40 can be deflected the full thickness of a patella, shown at 44 in FIG. 3, so that the bone-gripping member 18 is spaced a greater distance from the patella bone-facing surface 24. This distance is shown at $d_2$ in FIG. 3. The free end 40 of the cantilever spring member 16 can also be deflected to an intermediate position, shown in FIG. 4, wherein the patella bone facing surface 24 is flat against the resected posterior surface 46 of a patella 44 and the bone-gripping member 18 is pressed tightly against the anterior surface 48 of the patella 44. In this intermediate position, the bone-gripping member 18 is spaced an intermediate distance from the patella bone-facing surface 24. This intermediate distance is shown in FIG. 4 at $d_3$. As can be seen from comparing FIGS. 2-4, $d_1$ is less than $d_3$ which is less than $d_2$. It should be understood that although $d_1$ is greater than zero in the illustrated embodiment, in a patella drill guide incorporating the principles of the present invention, $d_1$ could be zero; that is, the tip of the bone-gripping member 18 could contact the patella bone-facing surface 24 of the base portion 14 when the cantilever spring member 16 is in its relaxed position. It should also be understood that absolute values for the distances $d_2$ and $d_3$ will vary from patient to patient.

Figure 3:
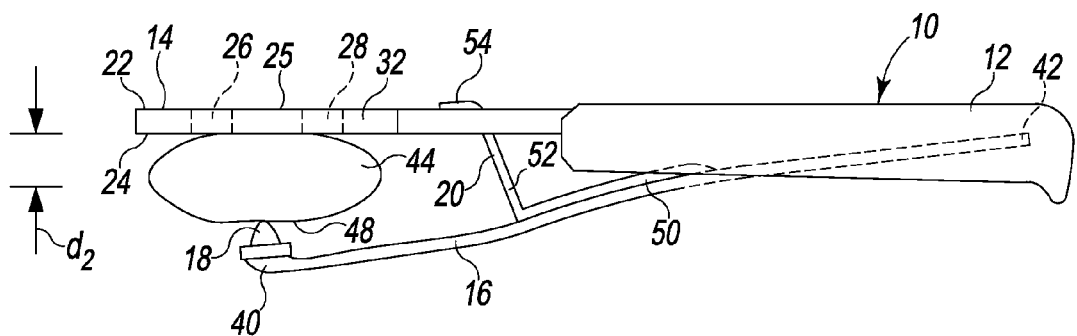
FIG. 3 is a side elevation view of the patella drill guide of FIGS. 1-2, shown clamping an unresected patella.

In the first illustrated embodiment, the bone-gripping member 18 at the free end 40 of the cantilever spring member 16 is moved between the relaxed position shown in FIGS. 1-2 to the deflected positions shown in FIGS. 3-4 by activation of the deflector 20 and resultant flexing of the cantilever spring member 16. The illustrated deflector 20 has a portion 50 that rests against a surface of the cantilever spring member 16, extending from a position outside of the handle 12 to a position within the handle 12. The illustrated deflector 20 also has a divergent portion 52 that diverges away from the cantilever spring member. 16. In the first illustrated embodiment, the divergent portion 52 extends through an aperture 56 (shown in FIG. 1) in the base portion 16 to an operating flange 54 that is spaced from and above the plane of the top surface 25 of the base portion 16. In use, the deflector 20 is activated by pressing against the flange 54 to overcome the spring force of the cantilever spring member 16 that biases the bone gripping member 18 toward the patella bone-facing surface 24. The deflector 20 flexes the cantilever spring member 16 to thereby increase the distance between the bone-gripping member 18 and the flat patella bone-facing surface 24. Once the patella drill guide is properly positioned with respect to the patella, the flange 54 is released and the spring force of the cantilever spring member 16 forces the bone-gripping member 18 and the patella bone-facing surface 24 toward each other, thereby clamping the patella between the bone-gripping member 18 and the patella bone-facing surface 24.

When the first illustrated clamping patella drill guide 10 is mounted on a resected patella as shown in FIG. 4, the single contact location between the single spike bone-gripping member 18 and the anterior surface 48 of the patella 44, and the lack of any bone-gripping spikes acting against the posterior resected 46 surface of the patella 44 allows for relative rotation or pivoting between the patella 44 and the clamping patella drill guide 10. This relative rotation or pivoting is about an axis that extends through the bone-gripping member 18 and the base portion 14; in the illustrated embodiment, the bone-gripping member is oriented so that this axis of rotation, shown at 58 in FIG. 4, is perpendicular to the plane of the patella bone-facing surface 24 of the base portion 14.

Since the orientation of the aligned bores 26, 28, 30 with respect to the patella changes as the base portion 14 is pivoted about the axis 56, and since the locations of the bores 26, 28, 30 correspond with the location of the mounting pegs on the implant component, the option of pivoting or rotating the base while it is clamped to the patella is advantageous, particularly for patella implant components that have anatomic or asymmetric articulation surfaces. The surgeon may adjust the orientations of the bores 26, 28, 30 intraoperatively and thereby optimize the orientation of the articulation surface of the patella implant component. To maximize this advantage, it may be desirable to provide a patella trial component that may be selectively mounted on the top surface 25 of the base portion 14 of the clamping drill guide 10. With such an assembly, the surgeon may ensure through trialing that the orientation of the articulation surface is optimized prior to drilling the holes to receive the mounting pegs.

Variations of the above-described structure are available for achieving the advantages of the present invention. Some variations are illustrated in alternative embodiments in FIGS. 5-12. In these embodiments, parts similar to those described above for the first embodiment are labeled with the same reference numbers as used in the above description and in FIGS. 1-4, followed by the letter "A" for the second embodiment, the letter "B" for the third embodiment, the letter "C" for the fourth embodiment, the letter "D" for the fifth embodiment and the letter "E" for the sixth embodiment. Unless a specific structure is described below, it should be assumed that the above description applies to like-numbered parts.

Figure 5:
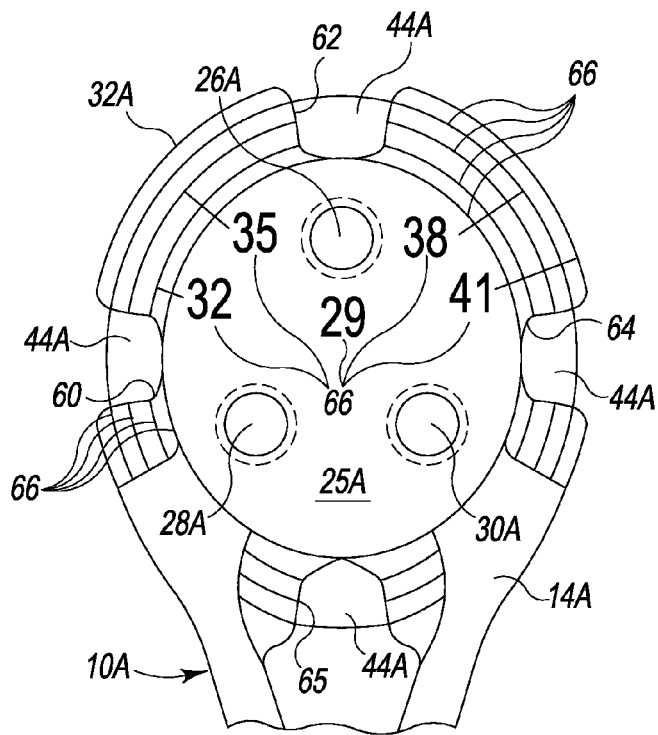
FIG. 5 is a top plan view of an alternative embodiment of one end of a patella drill guide incorporating the principles of the present invention.

In the second illustrated embodiment shown in FIG. 5, the top surface 25A and the edge 32A of the free end 22A of the base portion 14A include some additional features. In this embodiment, the edge 32A of the free end 22A includes a plurality of spaced cut-outs or recesses 60, 62, 64, 65 through which the resected posterior surface 46A of the patella 44A may be viewed. The top surface 25A of the base portion 14A includes sizing indicia 66 so that the surgeon can view the resected patella surface 46A juxtaposed with the sizing indicia 66 to determine the optimum size of patella implant component to be implanted. This embodiment is particularly beneficial if multiple sizes of patella implant components have commonly sized and positioned mounting pegs, so that the same drill guide 10A can be used for multiple sizes of patella implant components.

Figure 11:
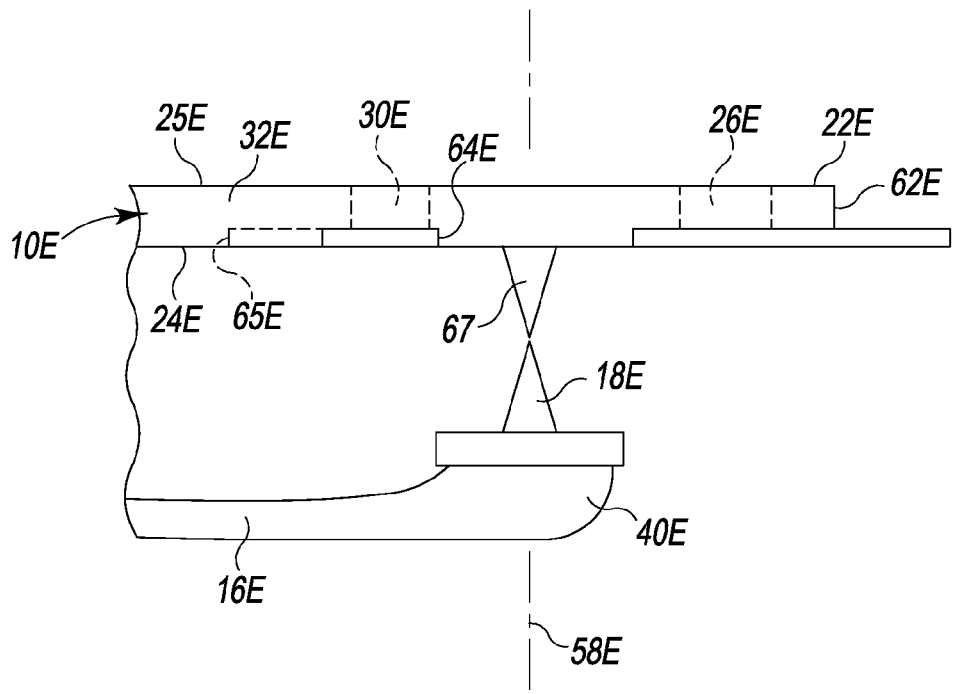
FIG. 11 is a side elevation of another alternative end portion of a patella drill guide, incorporating the features of the embodiment of FIG. 5 along with additional features.
Figure 12:
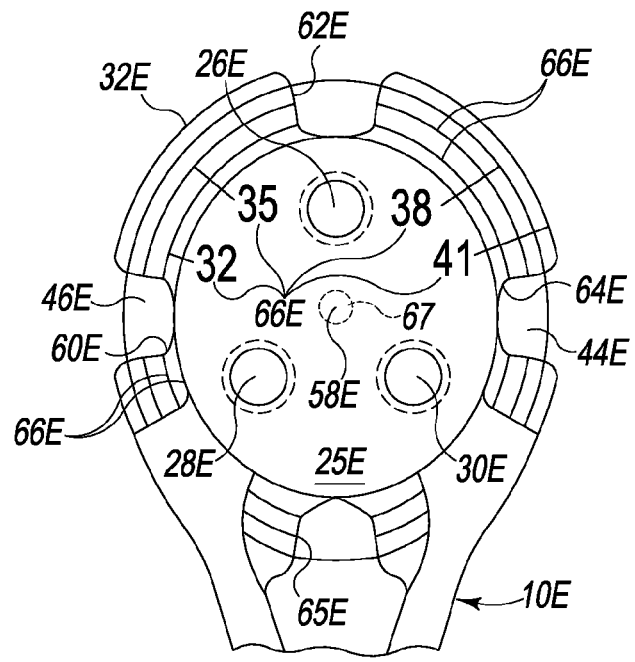
FIG. 12 is a top plan view of the base end portion of the patella drill guide of FIG. 10.

The sixth illustrated embodiment shown in FIGS. 11-12 is similar to the embodiment of FIG. 5. In the embodiment of FIG. 5, the base portion 14A has a constant thickness between the top surface 25A and the patella bone-facing surface 24A. In the alternative embodiment of FIGS. 11-12, the thickness of the base portion 14E varies: near the cut-outs or recesses 60E, 62E, 64E. 65E the thickness of the base portion 14E is less than the thickness near the drill guide bores 26E, 28E, 30E; for example, the thickness of the base portion 14E near the cut-outs or recesses 60E, 62E, 64E may be about 2 mm, while the thickness of the base portion 14E near the drill guide bores 26E, 28E, 30E may be about 6 mm. The varying thickness of the base portion may be advantageous in that the relatively thin areas around the cut-outs or recesses 60E, 62E, 64E, 65E make the size markings 66E more proximate to the patella bone surface 44E and therefore more readable. In addition, the thicker center section around the drill guide bores 26E, 28E, 30E may be useful in reducing the number of drill bits included in the instrument set. Typically, an instrument set would include a drill bit with a depth stop for drilling holes at the appropriate depth to receive pegs of other components, such as the femoral implant component. The thicker center section as the base portion 14E would allow this same drill bit, with the same depth stop, to be used to drill the holes for the patella implant component at the appropriate depth for the patella implant component.

The embodiment of FIGS. 11-12 also differs from that of FIG. 5 in that the base portion 14E also includes a bone-gripping component 67 in the embodiment of FIGS. 11-12. This bone-gripping component 67 comprises a single spike fixed to the base portion 14E and extending toward the bone-gripping member 18E on the end of the cantilever spring member 16E. With this embodiment, the entire assembly rotates as a unit about a longitudinal axis through the two bone-gripping elements 67, 18E when the spike 67 is pressed into the resected posterior surface of the patella 44E and the spike 18E is pressed into the native anterior surface of the patella. Other elements that fix the base to the resected posterior surface of the patella while allowing rotation of the base on the patella may be used; an example of such an alternative rotational mounting element is illustrated in the third illustrated embodiment.

Figure 6:
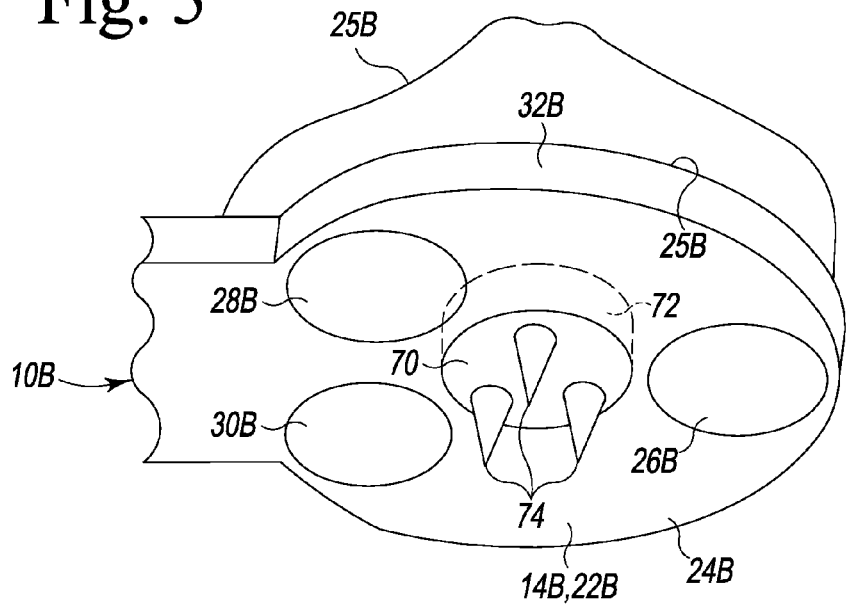
FIG. 6 is a perspective view of an alternative embodiment of one end of a patella drill guide incorporating the principles of the present invention.
Figure 7:
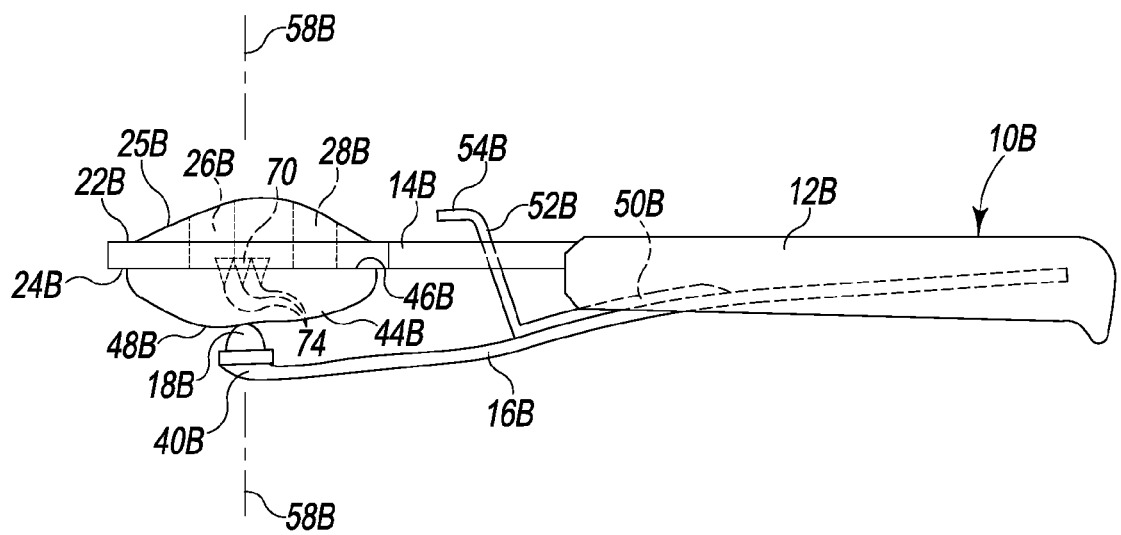
FIG. 7 is a side elevation view of the embodiment of the patella drill guide of FIG. 6, shown clamping a resected patella.
Figure 8:
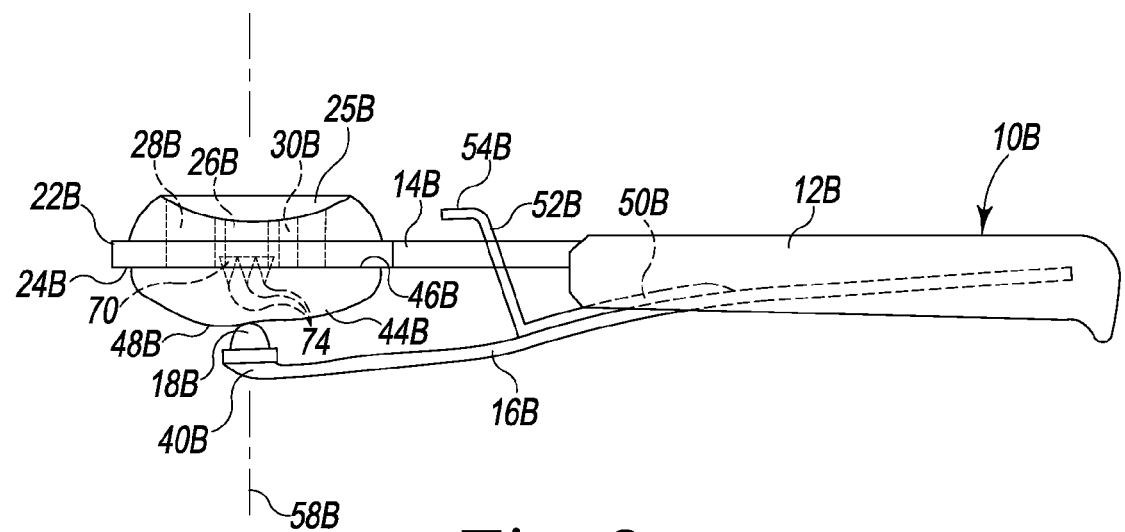
FIG. 8 is a side elevation view of the embodiment of the patella drill guide of FIGS. 6-7, shown with the patella drill guide pivoted 90 degrees with respect to the patella.

In the third illustrated embodiment shown in FIGS. 6-8, the top surface 25B comprises a trial articulation surface having a curved contour. In this embodiment, the drill guide bores 26B, 28B, 30B extend from the articulation surface 25B through the body of the base portion to the patella bone-facing surface 24B. The contoured articulation surface 25B may be an anatomic one, such as is disclosed in U.S. Pat. No. 6,074, 425, which is incorporated by reference herein in its entirety. The contoured articulation surface 25B may be shaped as disclosed in U.S. Pat. No. 7,972,383B2 and U.S. Pat. Publ. No. 2009-0326661 A1, which are incorporated by reference herein in their entireties. The contoured articulation surface may also comprise a sombrero-shaped or semi-sombrero-shaped surface. In general, the articulation surface 25B may be contoured to be shaped like the shape of the corresponding size of patella implant component.

Although the drill guide bores 26B, 28B, 30B extend through the trial portion in the third illustrated embodiment, variations are possible. For example, trials with reduced thicknesses to account for the thickness of the base portion 1, 14A, 14D, 14E may be provided in the surgical kit utilizing the embodiments illustrated in FIGS. 1-5 and 10-12. Such trials may have pegs that are sized and positioned to be received in the drill guide bores 26, 28, 30, 26A, 28A, 30A, 26D, 28D, 30D, 26E, 28E, 30E. With such an embodiment, the appropriately-sized trial can be selected, mounted on the top surface 25, 25A, 25D, 25E of the base portion 14, 14A, 14D, 14E with its mounting pegs received in the drill guide bores 26, 28, 30 26A, 28A, 30A, 26D, 28D, 30D, 26E, 28E, 30E and its articulation surface exposed opposite the patella bone-facing surface 24. After the surgeon has completed trialing and ensured proper orientation of the drill guide bores, the trial can be removed and the mounting holes drilled into the patella through the drill guide bores.

The third illustrated embodiment utilizes features described in more detail in a U.S. Provisional Patent Application 61/540,040 entitled "Rotatable Patella Drill Guide," filed concurrently herewith by Richard Spencer Jones, Martin W. Roche and Abraham P. Wright which is incorporated herein in its entirety. Thus, the third illustrated embodiment may include an additional bone-gripping component, shown at 70 in FIGS. 6-8, which includes a substantially cylindrical pedestal portion 72 rotationally mounted in a cylindrical bore in the free end portion 22B of the base portion 14B and a plurality of conical spikes 74 extending outwardly toward the bone-gripping member 18B at the free end 40B of the cantilever spring member 16B.

As disclosed in that provisional patent application, the drill guide bores 26B, 28B, 30B may comprise two portions: a larger diameter portion through the patella trial portion and the aligned portions smaller diameter through the base portion 14B so that annular shoulders are defined at the junctions of the smaller and larger diameter portions. The diameters of the annular shoulders may correspond with the diameter of a collar portion of a depth-control bit, such as collar 38 of the drill bit 34 shown in FIG. 4. In use, the annular shoulders will limit movement on the drill bit 34 into the patella by serving as a stop for the collar portion 38 of the drill bit 34; the lengths of the smaller diameter portions of the drill guide bores 26B, 28B, 30 B in this embodiment, together with the length of the fluted portion 36 of the drill bit 34 thereby control the depth of the holes drilled into the patella. The depth generally corresponds with the lengths of mounting pegs on the patella implant component.

In the embodiment of FIGS. 6-8, the surgeon has the benefit of trialing the patella articulation and adjusting the orientation of the drill guide bores 26B, 28B, 30B prior to drilling the mounting holes into the patella. The orientation of the drill guide bores 26B, 28B, 30B may be adjusted by pivoting or rotating the base 14B about the additional bone-gripping component 70 which is fixed to the resected posterior surface 46B of the patella 44B; the articulation surface 25B, drill guide bores 26B, 28B, 30B, handle 12B, cantilever spring member 16B and bone-gripping member 18 all pivot or rotate with the base 14B, all about pivot axis 58B. For example, the articulation surface 25B, base 14B, drill guide bores 26B, 28B, 30B, handle 12B, cantilever spring member 16B and bone-gripping member 18 may be pivoted about pivot axis 58B from the position shown in FIG. 7 to that shown in FIG. 8, as well as to other positions, until the orientation of the articulating surface 25B is optimized. This optimization of the trial articulating surface 25B results in optimization of the orientation of the drill guide bores 26B, 28B, 30B so that the mounting pegs and articulation surface of the patella implant component are optimally oriented as determined through the trialing process.

Figure 9:
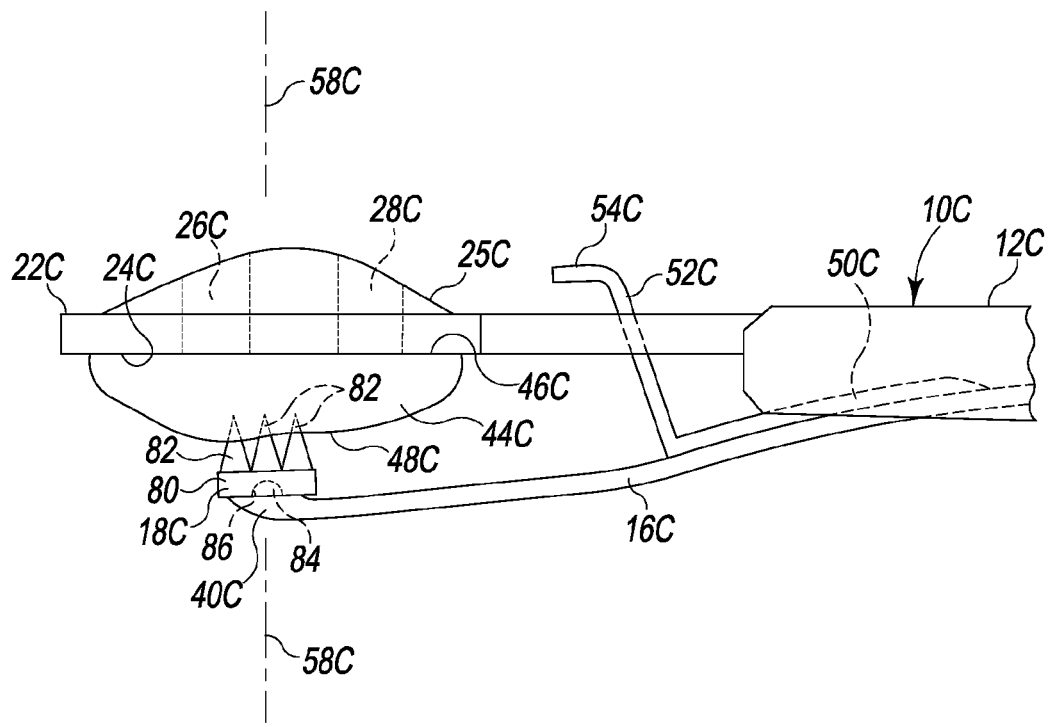
FIG. 9 is a side elevation view of an alternative embodiment of one end of a patella drill guide incorporating the principles of the present invention, shown clamping a resected patella.

Similar advantages are provided in the fourth alternate embodiment illustrated in FIG. 9. In the clamping drill guide 10C of the FIG. 9 embodiment, the bone-gripping member 18C at the free end 40C of the cantilever spring member 16C comprises a pedestal 80 and a plurality of conical spikes 82 extending outwardly from the pedestal 80 toward the patella bone-facing surface 24C of the base 14C. In this embodiment, the pedestal is not fixed relative to the free end 40C of the cantilever spring member 16C, but is rotatably mounted thereto through a complimentary spindle 84 and recess 86 about which the articulation surface 25C, base 14C, drill guide bores 26C, 28C, 30C, handle 12C and cantilever spring member 16C all pivot or rotate, all about pivot axis 58C.

In the embodiments of FIGS. 6-9, the base portion 14B, 14C and top articulation surface 25B, 25C are discrete, independent components that are connected to define an assembly. Although not illustrated, it should be understood that any suitable connection mechanism may be used to assemble these components such as complementary projections and recesses for a snap fit arrangement. It may be desirable to allow the surgeon to change the patella trial portions defining the top articulation surfaces 25B, 25C intraoperatively so that different sizes or shapes of articulation surfaces may be trialed on the same base portion 14B, 14C. The surgeon may also prefer to remove the trial portion defining the top articulation surface prior to drilling through the patella drill guide. It should also be understood that the base portion 14B, 14C from the patella bone-facing surface 24B, 24C to the top articulation surface 25B, 25C may instead comprise a single, integral or unitary component.

Figure 10:
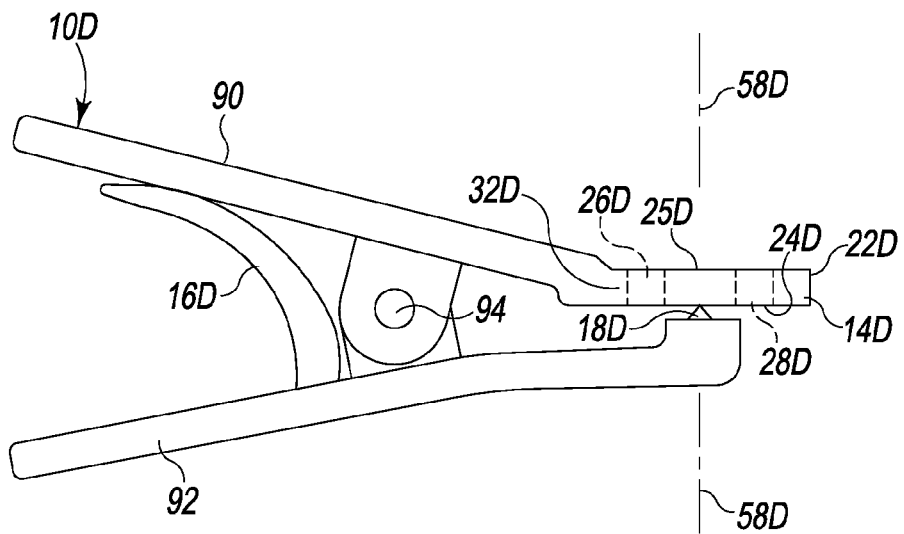
FIG. 10 is a side elevation view of another alternative embodiment of a clamping patella drill guide incorporating the principles of the present invention.

In the embodiment of FIG. 10, the clamping patella drill guide 10D comprises two arms 90, 92 connected by a hinge 94. One end of the cantilever spring member 16D is fixed to one arm 92 and another portion of the cantilever spring member 16D bears against a portion of the other arm 90 to bias the bone-gripping member 18D toward the flat patella bone-facing surface 24D. In this embodiment, the cantilever spring member 16 is flexed by squeezing the ends of the arms 90, 92 together, thereby pivoting the bone-gripping member 18D away from the patella bone-facing surface 24D.

In use, the surgeon would first prepare the patella by resecting the posterior surface of the patella to create a flat, planar surface, such as surface 46, 46B, 46C, 46E of patella 44, 44B, 44C, 44E. In the first illustrated embodiment and embodiments A-C and E, the surgeon would then select a clamping patella drill guide, such as clamping patella drill guide 10, 10A, 10B, 10C, 10E and position the patella bone-facing surface 24, 24A, 24B, 24C, 24E against the resected posterior surface 46, 46B, 46C, 46E while depressing the flange 54, 54B, 54C (not shown in FIGS. 11-12) to flex the cantilever spring member 16, 16B, 16C, 16E so that the free end 40, 40B, 40C, 40E is deflected enough so that the thickness of the patella can fit between the patella bone-facing surface 24, 24B, 24C, 24E and the bone-gripping member 18, 18B, 18C, 18E on the cantilever spring member 16, 16B, 16C, 16E. The flange 54, 54B, 54C can then be released. Once the flange is released, the spring action of the cantilever spring member 16, 16B, 16C, 16E will drive the bone-gripping member 18, 18B, 18C, 18E toward the patella bone-facing surface 24, 24B, 24C, 24E clamping the patella between these elements 18, 18B, 18C, 18E, 24, 24B, 24C, 24E (as well as spikes 67 and 74 in the embodiments of FIGS. 6-8 and 11-12).

In using the fifth illustrated embodiment of FIG. 10, the surgeon would press on the ends of the handles 90, 92 to separate the bone-gripping member 18D and the patella bone-facing surface 24D, thereby flexing the cantilever spring member 16D. The bone-facing surface 28D may be placed on the resected posterior surface of the patella and the handles released so that the spring action of the cantilever spring member 16D drives the bone-gripping member 18D toward the patella bone-facing surface 24D until it engages the anterior surface of the patella, clamping the patella between these elements 18D, 24D.

The surgeon may then pivot the base portion 14, 14A, 14B, 14C, 14D, 14E about pivot axis 58, 58B, 58C, 58D, 58E if desired until the surgeon is satisfied with the orientation of the drill guide bores 26, 26A, 26B, 26C, 26D, 28, 28A, 28B, 28C, 28D, 30, 30A, 30B, 30C, 30D, 26E, 28E, 30E. This pivoting action can be accomplished by moving the handle 12, 12B, 12C (not shown in FIGS. 11-12) or arms 90, 92. The surgeon may then hold the handle 12, 12A, 12B, 12C or arms 90, 92 with one hand (thereby holding both the patella and the drill guide with one hand) and use his free hand to drill the holes in the patella. Thus, a single person can stabilize the patella, hold the drill guide and perform the drilling. The depth of each hole into the patella may be set if the drill bit has a collar, such as collar 38 shown in FIG. 4.

When the holes are drilled, the clamping force may be released by pushing on the flange 54, 54B, 54C or by squeezing the arms 90, 92 to flex the cantilever spring member 16, 16B, 16C, 16D, 16E and deflect the bone-gripping member 18, 18B, 18C, 18D, 18E away from the anterior surface 48, 48B, 48C (not shown in FIGS. 11-12) of the patella 44, 44A, 44B, 44C, 44E. The patella implant component may be implanted, with its mounting pegs received in the drilled holes and its orientation optimized for proper tracking with respect to the femoral implant component.

All of the illustrated embodiments may be made of standard polymeric or metallic materials used in the field of surgical instruments, and may comprise assemblies of different such materials. Conventional manufacturing processes may be used. The invention is not limited to any particular material or manufacturing process unless expressly called for in the claims.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. Other features may be incorporated into the present invention, such as the features disclosed in U.S. Provisional Patent Application Ser. No. 61/540,053 entitled "Patella Drilling System", filed by Raymond E. Randle, Martin W. Roche and Abraham P. Wright. The complete disclosure of that patent application is incorporated by reference herein.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:

1. A patella drill guide for use in preparing a resected patellar bone surface to receive a prosthetic patellar implant, the patella drill guide comprising:
   a handle having a proximal end, a distal end, a longitudinal axis extending between the proximal and distal ends, a top surface, a bottom surface and an aperture extending between the top and bottom surfaces;
   a base portion extending from the handle to a free distal end having a flat patella bone-facing surface, and a trial articulation surface opposite and spaced from the flat patella bone-facing surface, the trial articulation surface having a curved contour;
   an independent bone-gripping portion assembled with the base portion at the free distal end;
   a plurality of spaced drill guide bores extending from the trial articulation surface through the base portion to and through the flat patella bone-facing surface;
   a cantilever spring member having one end fixed to the handle and an opposite free distal end aligned with the flat patella bone-facing surface;
   a bone-gripping member at the free distal end of the cantilever spring member and having a portion extending outward from the cantilever spring member toward the flat patella bone-facing surface of the base portion; and
   a deflector engaging a portion of the cantilever spring member between the two ends of the cantilever spring and extending through the aperture in the handle;
   wherein:
   the cantilever spring member has a relaxed position wherein there is a first distance between the bone-gripping member of the cantilever spring member and the flat patella bone-facing surface of the base portion;
   the cantilever spring member has a deflected position wherein the bone-gripping member of the cantilever spring member is spaced a second distance away from the flat patella bone-facing surface of the base portion;
   the second distance is greater than the first distance; and
   activation of the deflector moves the bone-gripping member of the cantilever spring member from the relaxed position to the deflected position.

2. The patella drill guide of claim 1 wherein when the patella drill guide is configured to be mounted on a patella, and the patella drill guide is rotatable with respect to the patella about an axis extending through the bone-gripping member and the base portion when mounted on a patella.

3. The patella drill guide of claim 2 wherein the axis of rotation is substantially perpendicular to the plane of the flat patella bone-facing surface and substantially parallel to the central longitudinal axis of the drill guide bore.

4. The patella drill guide of claim 1 wherein the bone-gripping component assembled with the base portion is rotatable with respect to the base portion.

5. The patella drill guide of claim 4 wherein the bone-gripping component on the base portion comprises a plurality of spikes.

6. The patella drill guide of claim 5 wherein the bone-gripping member at the free end of the cantilever spring member comprises a plurality of spikes.

7. The patella drill guide of claim 1 wherein the trial articulation surface and the flat patella bone-facing surface comprise discrete components assembled to define a combination patella drill guide and trial.

8. The patella drill guide of claim 1 wherein:
   the bone-gripping member at the free end of the cantilever spring member comprises a pedestal and a plurality of spikes extending outward from the pedestal; and
   the cantilever spring member is pivatably connected to the bone-gripping member so that the handle, the free end of the base portion and the cantilever spring member are pivotable with respect to the bone-gripping member.

9. The patella drill guide of claim 1 wherein the first distance is greater than zero.

10. The patella drill guide of claim 1 wherein the first distance is zero.

* * * * *